(12) United States Patent
Tottewitz et al.

(10) Patent No.: US 7,806,009 B2
(45) Date of Patent: Oct. 5, 2010

(54) IMMERSION TUBE FOR A MEASURING PROBE

(75) Inventors: Michael Tottewitz, Karlsdorf-Neuthard (DE); Daniel Caderas, Lohn (CH)

(73) Assignee: Mettler-Toledo AG, Greifensee (CH)

( * ) Notice: Subject to any disclaimer, the term of this patent is extended or adjusted under 35 U.S.C. 154(b) by 651 days.

(21) Appl. No.: 11/763,780

(22) Filed: Jun. 15, 2007

(65) Prior Publication Data

US 2008/0047343 A1    Feb. 28, 2008

(30) Foreign Application Priority Data

Jun. 23, 2006    (EP) .................................. 06115981

(51) Int. Cl.
   *G01D 21/00*    (2006.01)
(52) U.S. Cl. ........................................................ 73/866
(58) Field of Classification Search ................ 73/866.5, 73/86, 863.85
   See application file for complete search history.

(56) References Cited

U.S. PATENT DOCUMENTS

| | | | |
|---|---|---|---|
| 3,926,229 A | 12/1975 | Scholle | |
| 4,329,649 A | 5/1982 | Scoates | |
| 5,011,587 A | 4/1991 | Schmidt | |
| 5,296,197 A | 3/1994 | Newberg et al. | |
| 5,460,041 A | 10/1995 | Andes et al. | |
| 5,746,835 A | 5/1998 | Turner et al. | |
| 6,131,473 A | 10/2000 | Hoffman et al. | |
| 6,422,248 B1 | 7/2002 | Furst et al. | |
| 6,517,775 B1 | 2/2003 | Wang et al. | |
| 6,640,658 B1 | 11/2003 | Guerrero et al. | |
| 6,773,678 B2 | 8/2004 | Cummings et al. | |
| 6,860,162 B1 | 3/2005 | Jaeger | |
| 6,899,317 B2 * | 5/2005 | Brady et al. ................. | 251/264 |
| 2003/0019308 A1 | 1/2003 | Oppermann et al. | |
| 2005/0155408 A1 * | 7/2005 | Weyl et al. ................. | 73/23.31 |
| 2005/0211281 A1 | 9/2005 | Caderas | |
| 2005/0229727 A1 | 10/2005 | Caderas | |

FOREIGN PATENT DOCUMENTS

| | | |
|---|---|---|
| CH | 486906 A | 4/1970 |
| CH | 673783 A5 | 4/1990 |
| DE | 3709019 A1 | 9/1988 |
| DE | 3940948 A1 | 6/1991 |

(Continued)

*Primary Examiner*—Robert R Raevis
(74) *Attorney, Agent, or Firm*—Standley Law Group LLP (57) ABSTRACT

An immersion tube for a measuring probe of a type where a sensor element is arranged at the end of the measuring probe has a sleeve and an end piece. The end piece includes a plug, a connector piece, and a protector basket arranged between the plug and the connector piece. The connector piece connects the end piece to the sleeve and has an internal diameter that is enlarged relative to the internal diameter of the protector basket. The enlarged internal diameter portion ends at a circular internal step that can be seat for a sealing means, can provide a circular sealing lip, or both. A breakthrough opening on the protector basket is arranged perpendicular to the longitudinal axis of the immersion tube, whereby the sensor element which in operation is located in the protector basket can be brought into direct contact with a measurement medium. All surfaces and edges of the immersion tube which are exposed to the measurement medium during operation are smooth and rounded.

12 Claims, 4 Drawing Sheets

FOREIGN PATENT DOCUMENTS

| | | |
|---|---|---|
| DE | G9202350.9 U1 | 4/1992 |
| DE | 19546266 C2 | 6/1997 |
| DE | 19720504 A1 | 11/1998 |
| DE | 19723681 A1 | 12/1998 |
| DE | 19843553 A1 | 4/2000 |
| DE | 10024564 A1 | 11/2001 |
| EP | 0106858 B1 | 5/1984 |
| EP | 0372121 B1 | 6/1990 |
| EP | 0414032 A1 | 2/1991 |
| EP | 0545177 A1 | 6/1993 |
| EP | 0590290 A1 | 4/1994 |
| EP | 0882896 A1 | 12/1998 |
| JP | 57-122348 A | 7/1982 |
| JP | 3-269255 A | 11/1991 |
| JP | 10-19835 A | 1/1998 |
| WO | 83/03778 A1 | 11/1983 |

\* cited by examiner

IMMERSION TUBE FOR A MEASURING PROBE

CROSS-REFERENCE TO RELATED APPLICATIONS

This application claims a right of priority under 35 USC §119 from European patent application 06115981.0, filed 23 Jun. 2006, the content of which is incorporated by reference as if fully recited herein.

TECHNICAL FIELD

An immersion tube as a receptacle for a measuring probe represents a part of a measuring probe housing.

BACKGROUND OF THE ART

Measuring probes are used to determine various chemical and/or physical parameters of a medium such as for example the concentration of different substances, the pH value or the turbidity of a medium. Measuring probes of this kind often have an elongated body made for example of glass or a plastic material with a sensor element located at the end. To protect a measuring probe from getting damaged, measuring probes operating in a technical plant are usually arranged in a measuring probe housing. The known state of the art includes static probe housings as well as retractable probe housings with or without a treatment chamber.

Among others, measuring probe housings with immersion tubes are known which have a perforated protector basket in which the sensor element of the measuring probe is located during operation. The protector basket ends in a plug that faces towards the medium. The plug represents an important safety feature, because it allows a container that holds the medium to be sealed off against the ambient environment even when the immersion tube is retracted from the medium, and in the case of a retractable housing with treatment chamber, the plug allows the sensor element to be cleaned, calibrated and/or conditioned without the problem that treatment medium could escape from the measuring probe housing into the process medium, or that the process medium could enter into the measuring probe housing.

Depending on the field of application, different characteristics are required of a measuring probe housing or of the immersion tube to be installed in the housing. In particular for applications in the pharmaceutical industry, in the food industry and/or in biotechnology, a hygienic measuring probe housing would be desirable which would by design prevent germs and/or bacteria as well as residues of the process medium from attaching themselves to the inside or the surface, but would at the same time be safe and easy to handle.

It has been found that even when sterilizable materials are used such as stainless steel, or certain polymers such as Teflon, it is still possible that due to the design configuration, germs, bacteria and/or residues of process medium can attach themselves to or accumulate on the immersion tube and in particular on the protector basket, on the seals between the protector basket and the measuring probe and/or the seats for the seals. The accumulation or the attachment is helped by the formation of pockets and/or gaps which occurs on or inside the immersion tube already in the course of the technically demanding manufacturing process.

A special form-fitting seal is disclosed in published US application 2003/0019308 A1, by Oppermann ("Oppermann '308"), for an immersion tube without a safety plug and with a protector basket that is open at the end facing towards the medium. After the measuring probe has been inserted, this form-fitting seal forms a pressure fit in the opening and seals the interior space of the measuring probe housing without leaving a gap against the process medium. While the immersion tube according to this disclosure ensures a gap-free seal between the process space or process medium and the interior space of the measuring probe housing, it suffers from the drawback that in taking the measuring probe out of the housing, it is possible for process medium to escape from the process through the housing, or it is also possible for the sensor element to be damaged or destroyed during the process by particles or contaminations which can enter the protector basket through the terminal opening.

Oppermann '308 discloses a special type of molded seal for an immersion tube without a safety plug and with an protector basket, which is open at the end of the immersion tube facing a medium. This molded seal forms a press fit in the opening after insertion of the measuring probe and provides a gapless seal between the interior of the measuring probe housing and the process. The disclosed immersion tube does provide a gapless between the measuring probe housing and the process, but when the measuring probe is extracted from the measuring probe housing medium could leak from the process through the measuring probe housing or the sensor element could be damaged or destroyed by particles or contaminations, which can pass through the terminal opening into the protector basket.

It is therefore an object to develop a safe and hygienic immersion tube, as well as a measuring probe housing in which an immersion tube is arranged.

SUMMARY OF THE INVENTION

An immersion tube as a receptacle for a measuring probe that has a sensor element arranged at the end comprises a sleeve and an essentially monolithic end piece. The end piece comprises a plug, a connector piece, and a protector basket arranged between the plug and the connector piece. The end piece can be connected to the sleeve by means of the connector piece, wherein the latter has an enlarged internal diameter in relation to the internal diameter of the protector basket. The transition between the elements of different internal diameter is configured as a circular ledge or step which can either serve as a seat for a known sealing means such as for example an O-ring seal and/or can be designed as an elastic sealing lip.

The protector basket has at least one breakthrough opening arranged perpendicular to the longitudinal axis of the immersion tube, whereby during operation a measurement medium can be brought into contact with the sensor element that is to be arranged in the protector basket.

The immersion tube is distinguished in that the surfaces and edges, in particular those of the protector basket, which during operation are exposed to the measurement medium are smooth and rounded.

Furthermore, the internal surface of the protector basket that borders on the plug can be configured with a downward slope in at least one outward direction, so that the measurement medium which during operation enters into the protector basket can pass quickly through the latter and can run off quickly when the measuring probe housing is removed from the medium, and no residues of the medium can accumulate in the protector basket.

Configuring the immersion tube substantially in two parts has the advantage, that the monolithic end piece and in particular the protector basket can be produced with simple, state-of-the-art processes and that it obviates the need for complicated undercuts of the kind that were often necessary in previous designs in order to provide seats for sealing means. Furthermore, a later insertion and/or attachment of the plug is eliminated, as the protector basket as well as the connector piece can be worked out and formed directly in the end piece by machining from the side of the connector piece. In addition, the rounded, smooth surfaces and edges prevent the attachment and/or accumulation of germs, bacteria and residues of a medium.

An immersion tube as described herein is distinguished by the fact that the connection between the sleeve and the end piece is preferably an integral material connection which is produced for example by welding. An integral material connection between the sleeve and the end piece is important to ensure that the immersion tube is stable and free of leaks. The integral material connection is matched to the material being used for the immersion tube and can be produced for example by welding, adhesive bonding, soldering or also by pouring or spraying.

In one embodiment, the outside diameter of the end of the sleeve that faces towards the end piece is about equal to the internal diameter of the connector piece, so that the sleeve can be inserted into the connector piece. Preferably, the part of the sleeve that is not in contact with the connector piece has an enlarged outside diameter, so that after the immersion tube has been assembled, it has a substantially uniform outside diameter.

A sleeve ending can be arranged in the connector piece in such a way that at the inside of the immersion tube a circular seat is created for a sealing means which is delimited on one side by the circular step between the connector piece and the protector basket and on the other side by the sleeve ending.

In a preferred embodiment, the sleeve ending that faces towards the end piece has an enlarged internal diameter which is about equal to the internal diameter of the connector piece. In the assembled immersion tube, the ends of the sleeve and of the connector piece adjoin each other directly. For stability and to form a seat for a sealing means, an internal sleeve with an outside diameter about equal to the internal diameter of the connector piece can be arranged in the connector piece and in the adjoining sleeve ending in such a way that a circular seat for a sealing means is created between the internal sleeve and the step in the end piece. The internal sleeve can further serve as a connecting aid and as a means of stabilizing and/or sealing the seam between the end piece and the sleeve.

In a further embodiment, the measuring probe housing has a circular sealing lip whose free end is shaped as a sharp edge. When a measuring probe is installed in the immersion tube, the sealing lip preferable meets the measuring probe at a clearance angle α>0°.

In a further embodiment, the measuring probe housing includes a sealing means as well as a sealing lip. This configuration is particularly advantageous as the sealing lip can function as a second seal and/or as a wiper, so that in removing the measuring probe from the measuring probe housing and/or in retracting the measuring probe into a treatment chamber, the medium clinging to the probe is wiped off by the sealing lip.

A probe housing includes an immersion tube of the disclosed embodiments and a measuring probe that is arranged in the immersion tube in a way that allows the probe to be exchanged. The measuring probe housing can be configured as a static housing or as a retractable housing.

BRIEF DESCRIPTION OF THE DRAWINGS

Several embodiments of an immersion tube and a measuring probe housing with an immersion tube are described below, with reference to the appended figures, in which identical elements have the same reference symbols, and in which.

DETAILED DESCRIPTION OF PREFERRED EMBODIMENTS

Figure 1:
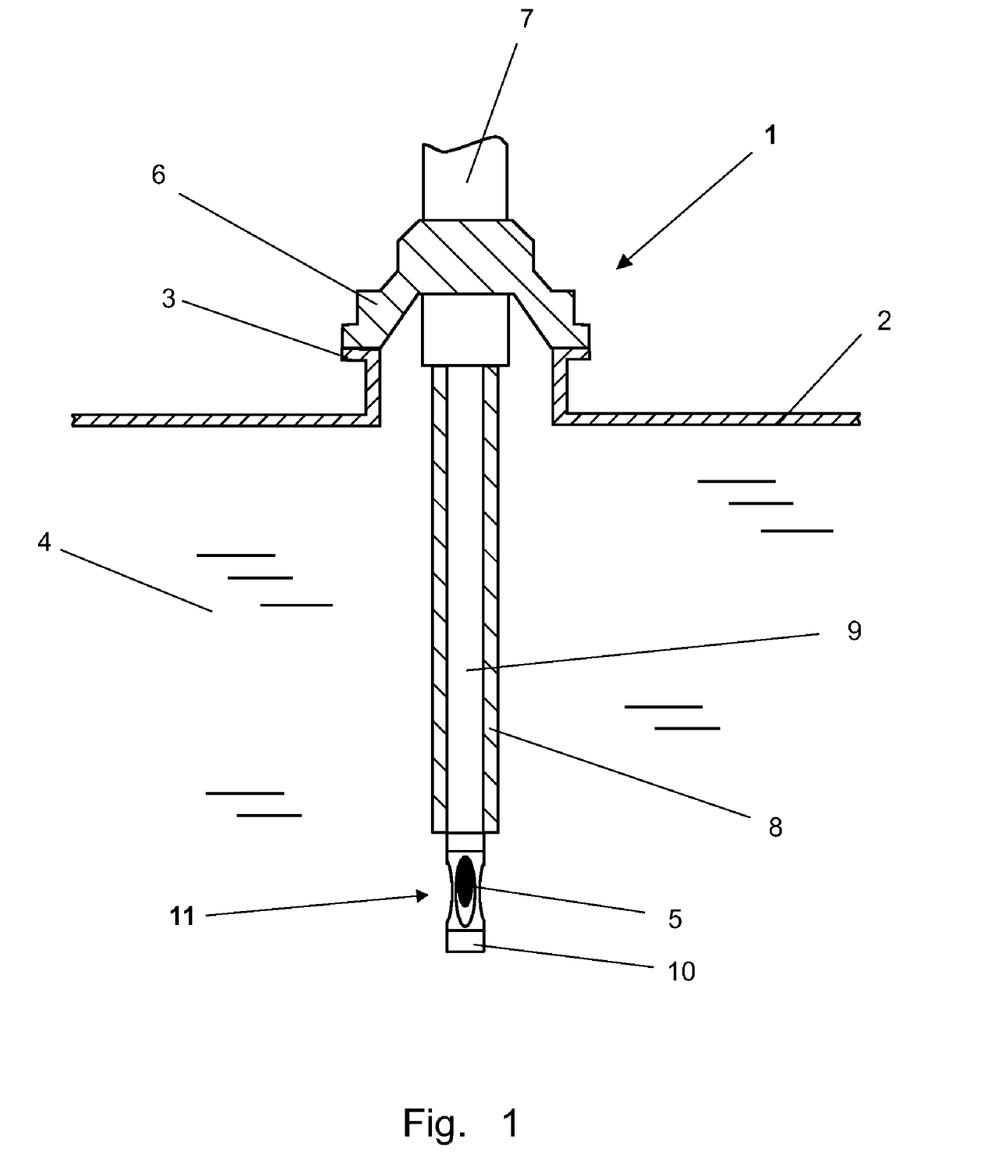
FIG. 1 is a side sectional view of a measuring probe housing with an immersion tube arranged in a container.

FIG. 1 schematically illustrates a static measuring probe housing arranged in a container, seen here in a sectional view. To indicate the container, only a part of a wall 2 with a connector socket 3 is shown in this drawing. The container can, for example, be a pipe conduit, a reactor vessel, or any other container. The container holds a measurement medium 4 in which a measuring probe 5 is immersed which is arranged in a measuring probe housing 1. The only part of the measuring probe 5 that is visible here is a sensor element located at the end of the measuring probe.

The measuring probe housing 1 consists of a process connector 6 which can be connected through appropriate means such as for example clips or couplings to the connector socket 3 on the container. The known state of the art includes a variety of process couplers, in particular hygienic couplers, such as for example the Varivent-, TriClamp-, or milk pipe coupler, and the coupling connection is therefore not discussed in further detail.

Arranged above the process connector 6 and thus outside of the container is a handle 7 which among other functions contains the electronics required for the operation of the measuring probe 5. Below the process connector 6 and thus inside the container is an elongated enclosure 8 which belongs to the measuring probe housing 1 and contains the immersion tube 9 and the measuring probe 5. FIG. 1 shows as an example a static measuring probe housing 1, but a comparable arrangement can also be realized with a retractable probe housing. A retractable probe housing is designed in a way that allows the measuring probe to be exchanged also during operation.

At the end that faces towards the measurement medium 4, the immersion tube 9 has a perforated protector basket 11 and a solid plug 10. The protector basket 11 is designed to hold the sensor element of the measuring probe 5 during operation, so that the sensor element can enter into contact with the measurement medium 4.

The design configuration of a static measuring probe housing as shown in FIG. 1 represents substantially a probe housing of the known state of the art. Besides static probe housings 1, there are also retractable housings known which allow the immersion tube 9 and the measuring probe 5 inside it to be pulled back from the container, for example into a treatment- and/or calibration chamber where the measuring probe 5 can be rinsed independently of the measurement medium 4 with a suitable treatment medium, or where it can be calibrated and/or conditioned. For treatment media, one can use liquids as well as gases, and it would furthermore be possible for example to evacuate the treatment chamber, in particular for removing possible residues of the treatment medium. Especially in connection with retractable probe housings, the plug 10 at the end of the immersion tube 9 is of importance, because it can safely close off the enclosure 8 of the retractable probe housing when the immersion tube 9 is pulled back, whereby any exchange of medium between the retractable probe housing, the container, and the ambient environment is prevented.

Figures 2, 3:
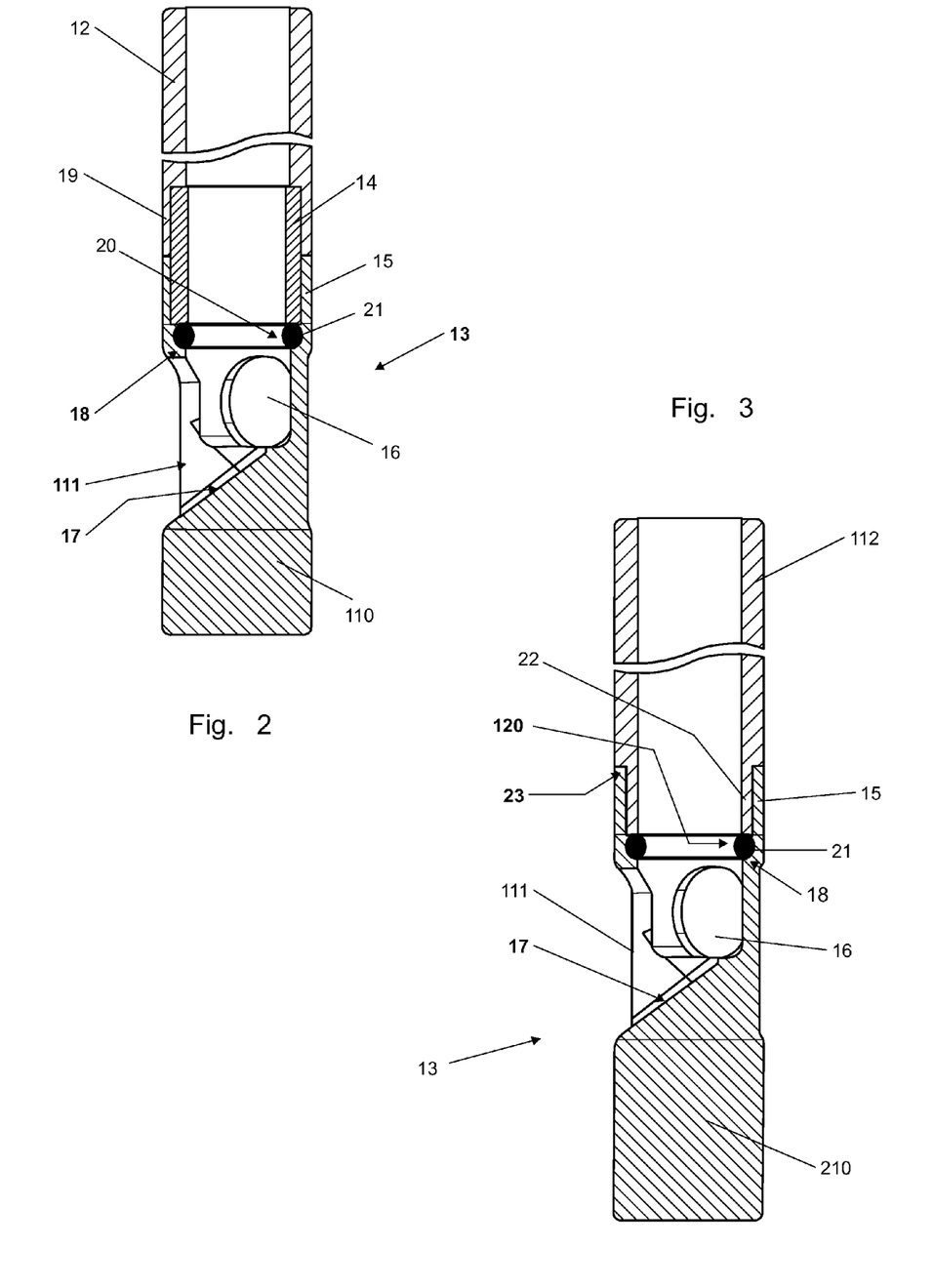
FIG. 2 is side sectional view of an immersion tube with a sleeve and an end piece which are connected by means of an internal sleeve.
FIG. 3 is a side sectional view of an immersion tube with a sleeve and an end piece which are directly connected to each other.

FIG. 2 shows a part of an immersion tube with a sleeve 12, an end piece 13, and an internal sleeve 14 as a connecting aid. The end piece 13 which is normally designed as a single piece has in essence a connector piece 15, a protector basket 111 connected to the connector piece 15, and a solid plug 110 located at the end. The protector basket in this embodiment is formed in essence by three material connections extending between the connector piece 15 and the plug 110.

The immersion tube can easily be fitted to the dimension of the measuring probe that is to be used by adapting the length of the sleeve 12 to the length of the measuring probe. The known measuring probes have a length of 120 mm as well as lengths between 225 and 425 mm, among others. The outside diameters of the measuring probes are normally standardized so that uniform sleeves 12 in different lengths can be connected to suitable end pieces. This modular design of the immersion tubes simplifies and optimizes their production.

The protector basket 111 has at least one breakthrough opening 16 as well as an inclined surface 17 sloping downwards towards the outside. A protector basket of this design is used primarily in combination with optical sensors such as for example turbidity sensors or optical gas sensors and will be described in more detail in the context of FIGS. 5a to 5d.

The connector piece 15 has an enlarged internal diameter in comparison to the protector basket 111, so that a circular step 18 is formed. At the end that faces towards the end piece 13, the sleeve 12 has likewise an enlarged internal diameter which is essentially equal to the internal diameter of the connector piece 15.

The portions with enlarged internal diameters, the connector piece 15 and the end 18 of the sleeve 12 form a seat for the internal sleeve 14 whose outside diameter matches the inside diameter of the connector piece 15 and whose internal diameter equals the internal diameter of the rest of the sleeve 12 and the protector basket 111. The internal sleeve 14 is slightly shorter than the lengthwise dimension of this seat, so that at the end that faces towards the end piece 13 a further seating space 20 remains which is delimited by the step 18 and the internal sleeve 14 and serves to hold a sealing means 21, in particular an O-ring.

The sealing means 21 seals the interior of the immersion tube against the measurement medium that streams through the protector basket during operation.

The free ends of the connector piece 15 and the end of the immersion tube 19 adjoin each other directly and are integrally connected to each other in a suitable process such as for example welding. The internal sleeve 14 serves to reinforce the immersion tube wall, and it also serves as a connector means to provide a simple connection of the sleeve 12 to the end piece 13. The internal sleeve 14 further seals the connecting seam between the sleeve ending 19 and the connector piece 15 against the interior of the immersion tube.

FIG. 3 shows a further embodiment of an immersion tube consisting of an end piece 13 and a sleeve 112. The end piece 13 is substantially the same as the end piece of FIG. 2 and will therefore not be described in more detail, except that the plug 210 of this end piece is longer in comparison to FIG. 2.

The sleeve 112 has a uniform internal diameter. To connect the sleeve 112 to the connector piece 15, the end 22 of the sleeve 112 has a reduced outside diameter, so that a circular step 23 is formed on the outside. The outside diameter of the sleeve ending 22 is substantially equal to the internal diameter of the connector piece 15, so that the connector piece 15 can receive the sleeve ending 22. The free end of the connector piece 15 adjoins the step 23. The length of the sleeve ending 22 with the reduced diameter is slightly shorter than the connector piece 15, so that between the sleeve ending 22 and the step 18 a seat 120 is formed for a sealing means 21. The sleeve ending 22 and the connector piece 15 are integrally connected through a process that is appropriately selected for the material being used.

Both of the immersion tubes shown in FIGS. 2 and 3 have an integral connection between the end piece and the sleeve. The design concept with several parts allows in particular the seat for the sealing means to be produced in a very precise and simple way, for example by suitable machining of the sleeve as well as the end piece, without the need for complicated undercuts that occur in the known immersion tubes with plugs.

Figure 4A:
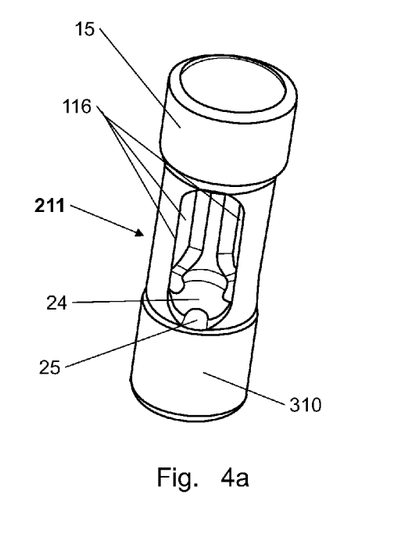
FIG. 4a is a perspective view of an end piece with a first protector basket.
Figure 4B:
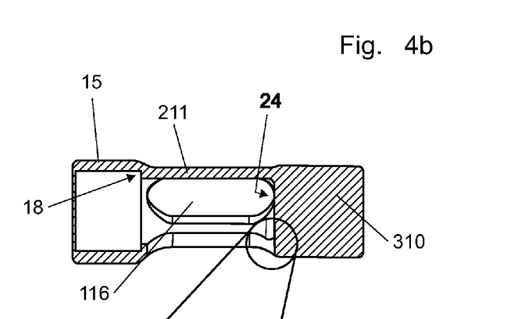
FIG. 4b is a side sectional view of the FIG. 4a end piece.
Figure 4C:
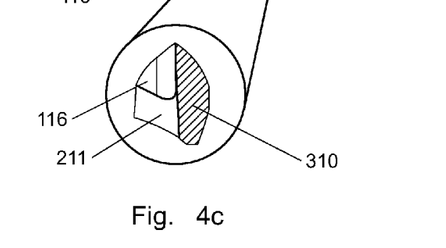
FIG. 4c is an enlarged view of a portion of FIG. 4b.
Figure 5A:
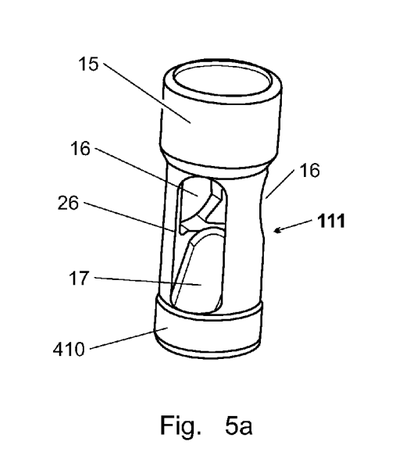
FIG. 5a is a perspective view of an end piece with a second protector basket.
Figure 5B:
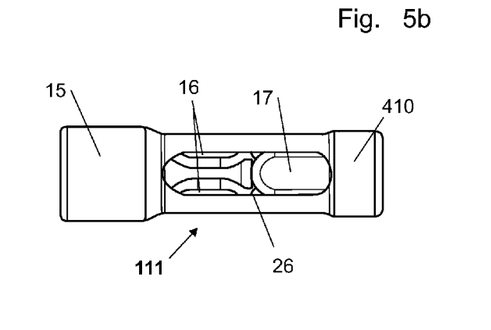
FIG. 5b is a side elevational view of the FIG. 5a end piece.
Figure 5C:
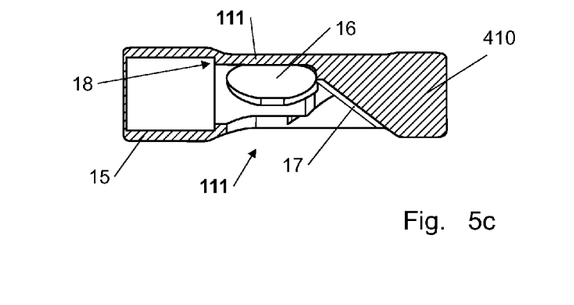
FIG. 5c is a side plan sectional view of the FIG. 5a end piece.
Figure 6:
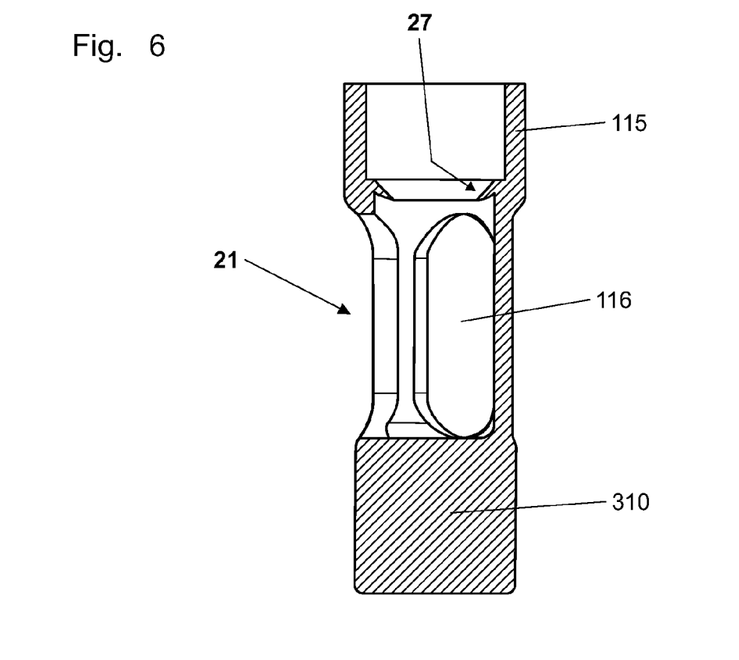
FIG. 6 is a side sectional view of an end piece on which a sealing lip is formed.

FIGS. 4 to 6 show detail views of different embodiments of the end piece. FIGS. 4a to 4c show an end piece designed to accommodate for example a pH measuring probe, and FIGS. 5a to 5c show an end piece designed to accommodate for example a turbidity sensor. FIG. 6 show an end piece on which a circular elastic sealing lip is formed. In the following, the FIGS. 4a to 4c are covered largely by a common description, and this also applies to FIGS. 5a to 5c. The end piece can be produced independently of the sleeve. Since the connector piece is short in relation to the overall length of the immersion tube, the protector basket can be made with high precision in a simple process, and all edges can be optimally rounded. Furthermore, it is possible to give the end piece a monolithic design, which avoids a subsequent step of attaching and/or fitting the plug and also avoids the associated consequence of an undefined gap between the immersion tube wall and the plug. The plug can be designed with different lengths depending on the application.

FIG. 4a shows a three-dimensional view of a monolithically designed end piece. The end piece has a plug 310, a protector basket 211 connected to the plug 310, and a connector piece 15 connected to the protector basket 211.

The protector basket 211 shown here has three breakthrough openings 116 which are arranged perpendicular to the longitudinal axis of the immersion tube and are equally spaced apart from each other. The breakthrough openings 116 are of substantially elliptical shape and have rounded edges (see also FIG. 4c).

The plug 310 borders on the protector basket 211, with the border surface 24 being slightly domed and sloping towards the outside, so that the measurement medium entering into the protector basket can easily run off and/or stream through the basket and will not collect and/or form a deposit in the basket. In addition to the dome-shaped curvature, the border surface has drain spouts 25 sloping down more strongly towards the outside, which are arranged at the middle of the breakthrough openings 116. All corners and edges in the protector basket 211 are rounded, so that the measurement medium cannot attach itself or form deposits, with the result that, e.g., bacterial growth or other deposits are substantially reduced.

The connector piece 15 again has an enlarged internal diameter in comparison to the protector basket 211 and can be joined to a sleeve through an integral material connection (see FIGS. 1 to 3).

The different internal diameters of the connector piece 15 and the protector basket 211 are shown clearly in the sectional drawing of FIG. 4b. This view also shows the circular step 18 which is formed between the connector piece 15 and the protector basket 211. The step 18 represents a part of the seat for the sealing means (see FIGS. 2 and 3).

FIG. 4c represents an enlarged detail of FIG. 4b and shows the rounded corners of a breakthrough opening 116 in the vicinity of the plug 310.

FIG. 5a represents a three-dimensional view of the end piece that has already been shown in FIGS. 2 and 3, wherein the plug 410 has a different length. The protector basket 111 in this example has three breakthrough openings 16, 26 which are arranged perpendicular to the axis of the immersion tube. The opening 26 has an elliptical shape, with the longer axis of the ellipse taking up almost the entire length of the protector basket 111. This breakthrough opening 26 provides a view of an inclined surface 17 which slopes downward towards the breakthrough opening 26 and towards the outside. The other breakthrough openings 16 are likewise elliptical and are designed somewhat smaller than the breakthrough opening 26.

FIG. 5b shows the end piece of FIG. 5a in a side view, and FIG. 5c shows the same end piece in a sectional view. The circular step 18 between the connector piece 15 and the protector basket 111 can be seen again in FIG. 5b.

The end pieces shown in FIGS. 4 and 5 can have the connector pieces shown in FIG. 2 or those shown in FIG. 3 and can be connected through them to a sleeve.

By connecting the sleeve and the end piece later the manufacturing process of immersion tubes with a plug is made significantly simpler, because this makes it possible to form the end piece monolithically. The complicated protector basket can be made in different versions with rounded edges, and the seat for the sealing means is provided only by the connection between the sleeve and the end piece, so that complicated undercuts and undefined gaps can be avoided.

FIG. 6 shows an end piece with a circular sealing lip 27 formed at the transition between a connector piece 115 and a protector basket 21. This embodiment is advantageous if the end piece consists of a polymer material such as for example Teflon, PVDF (polyvinylidene difluoride), PTFE (polytetrafluoroethylene) or PP (polypropylene). In this case, the end piece and the sealing lip 27 can be formed directly out of one piece in the manufacturing process. When a measuring probe is installed in the immersion tube, the sealing lip 27 is pressed tightly against the body of the measuring probe 21 and thereby seals the interior of the sleeve against the protector basket 21 and against a measurement medium. To ensure that the sealing lip 27 forms a sufficiently tight contact between the immersion tube and the measuring probe as required for hygienic applications, it is advantageous if the sealing lip 27 is designed so that it ends in a sharp edge, i.e., with a sharp edge angle. In addition, the clearance angle at which the sealing lip 27 meets the measuring probe should always be larger than 0°, so that when a measuring probe is in place, the sharp edge always lies tightly against the body of the measuring probe. This is intended to avoid the possibility of a ring gap forming between the body of the measuring probe and the sealing lip, where deposits could attach themselves. An end piece of this type can be connected to either version of a sleeve as shown in FIGS. 2 and 3. If an internal sleeve is used, the latter can be configured so that it fits precisely into the seating space that is formed between the sleeve and the connector piece.

Figure 7:
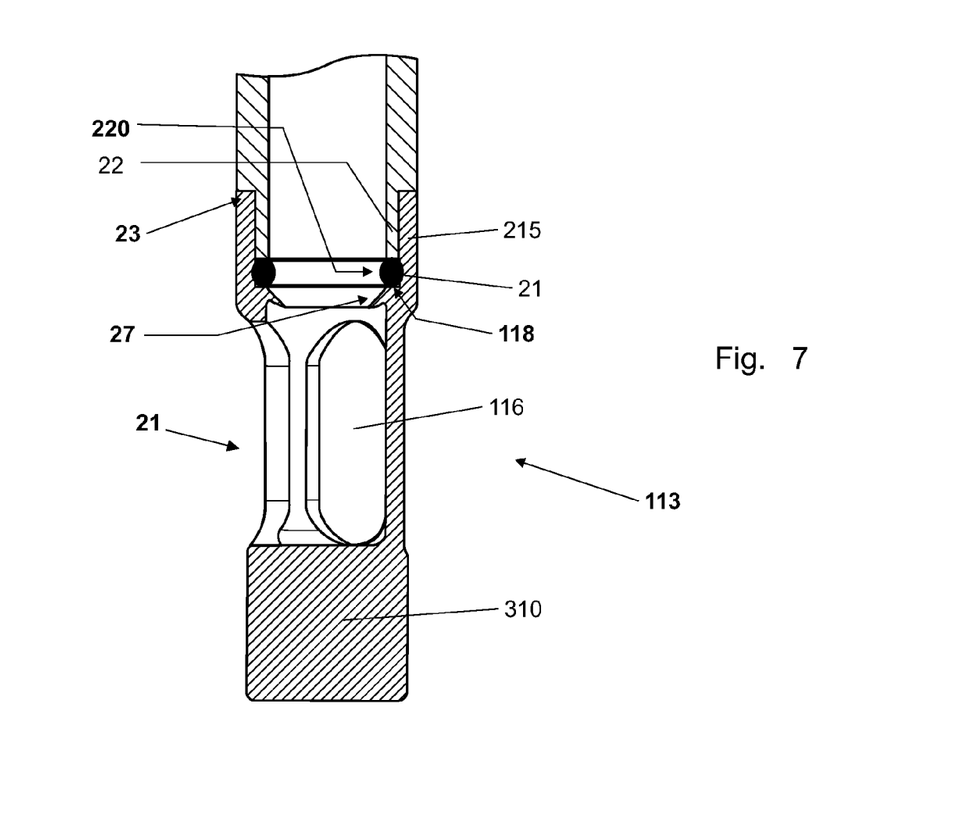
FIG. 7 is partial side sectional view of an immersion tube, with a sealing lip formed on the end piece and with a further sealing means.

FIG. 7 shows an immersion tube with an end piece 113 equipped with a sealing lip 27 and a further sealing means 21. The sealing lip 27, which has essentially the same characteristics as the sealing lip of FIG. 6, is arranged around the internal circumference of the connector piece 215 at the end that faces towards the protector basket 21. Above the sealing lip 27 (relative to the drawing), the connector piece 215 has a step 118 which forms part of a seat 220 for the sealing means 21. The seat 220 for the sealing means 21 is substantially equal to the one shown in FIG. 3. The embodiment illustrated in FIG. 7 is advantageous in that a sealing means in the form of a sealing lip 27 that is integrally connected to the end piece 113 is supplemented by an interchangeable sealing means 21. The interior of the immersion tube, and thus the measuring probe, are doubly protected against the penetration of the medium. In addition, the sealing lip 27 in this embodiment serves as a wiper, so that when the measuring probe is taken out of the probe housing and/or when the measuring probe is retracted into the treatment chamber, in particular in a retractable armature, the medium clinging to the measuring probe is wiped off.

Besides the embodiments described and illustrated, it is also possible to design end pieces with different state-of-the-art protector baskets. The end piece and the sleeve in the embodiments shown herein can be connected to each other, with the type shown in FIGS. 6 and 7 being particularly well suited for an immersion tube of a polymer material. Depending on the design of the sleeve ending that is to be connected to the connector piece, it is possible to use an internal sleeve, or the sleeve can be connected directly to the end piece.

What is claimed is:

1. A tube for immersing, in a liquid measuring medium, a measuring probe having a sensor element arranged at an end thereof, the immersion tube comprising:
    a sleeve; and
    an end piece, comprising a plug, a connector piece, and a protector basket arranged therebetween;
    the connector piece connecting the end piece to the sleeve and having an internal diameter that is enlarged relative to an internal diameter of the protector basket, the enlarged internal diameter ending at a circular internal step;
    the protector basket having at least one breakthrough opening, arranged perpendicular to a longitudinal axis of the immersion tube, so that an operatively-positioned sensor element of the measuring probe would be located in the protector basket in a manner that is in direct contact with the measurement medium; and
    wherein all surfaces and edges of the immersion tube that are exposed to the measurement medium during operation are smooth and rounded.

2. The immersion tube of claim 1, wherein:
    an internal surface of the protector basket which borders on the plug slopes downwardly towards the outside, in at least one direction.

3. The immersion tube of claim 1, wherein:
    the circular internal step provides a seat for a sealing means.

4. The immersion tube of claim 1, wherein:
    the circular internal step is configured as a circular sealing lip.

5. The immersion tube of claim 4, wherein:

a free end of the circular sealing lip is configured as a sharp edge, and the circular sealing lip meets the measuring probe, when seated in the immersion tube, at a clearance angle greater than 0°.

6. The immersion tube of claim 1, wherein:

the sleeve and the end piece are joined by an integral material connection.

7. The immersion tube of claim 1, wherein:

a sleeve ending of the sleeve faces towards the end piece, with an outside diameter substantially equal to the connector piece internal diameter.

8. The immersion tube of claim 7, wherein:

a rim of the sleeve ending and the circular internal step co-act to form a seat for a sealing means.

9. The immersion tube of claim 1, wherein:

a sleeve ending of the sleeve faces towards the end piece, with an internal diameter that is enlarged in comparison to an oppositely-facing part of the sleeve, the enlarged internal diameter being about equal to the connector piece internal diameter.

10. The immersion tube of claim 9, further comprising:

an internal sleeve, arranged in part inside each of the sleeve and the connector piece.

11. The immersion tube of claim 10, wherein:

a rim of the internal sleeve which faces towards the end piece and the circular internal step co-act to form a seat for a sealing means.

12. A measuring probe housing, comprising:

an immersion tube according to claim 1, with a measuring probe arranged interchangeably therein.

* * * * *